United States Patent
Makiuchi et al.

(12) 
(10) Patent No.: US 6,852,540 B2
(45) Date of Patent: Feb. 8, 2005

(54) CONTROL SERUM FOR DRY ANALYTICAL ELEMENT

(75) Inventors: Haijime Makiuchi, Saitama (JP); Hideaki Tanaka, Saitama (JP); Kaoru Terashima, Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/659,928

(22) Filed: Sep. 11, 2003

(65) Prior Publication Data

US 2004/0048324 A1 Mar. 11, 2004

Related U.S. Application Data

(63) Continuation of application No. 10/159,081, filed on May 29, 2002, now abandoned.

(51) Int. Cl.$^7$ .............................................. G01N 31/00
(52) U.S. Cl. .............................. 436/16; 436/8; 436/169; 436/174; 422/56
(58) Field of Search ............................. 436/8, 16, 174, 436/169; 422/56; 252/408.1; 435/4, 10–12

(56) References Cited

U.S. PATENT DOCUMENTS

| | | | | |
|---|---|---|---|---|
| 3,993,585 | A | * 11/1976 | Pinto et al. | .................... 436/13 |
| 4,123,384 | A | * 10/1978 | Hundt et al. | ................. 435/188 |
| 4,136,159 | A | * 1/1979 | Stone | ........................ 424/1.53 |
| 4,368,275 | A | * 1/1983 | Yanagihara et al. | ........... 521/52 |
| 4,900,665 | A | * 2/1990 | Terashima et al. | ............ 435/21 |
| 5,336,599 | A | * 8/1994 | Kitajima | ...................... 435/15 |
| 5,656,434 | A | * 8/1997 | Terano et al. | ................ 435/7.1 |
| 5,709,837 | A | * 1/1998 | Mori et al. | ................... 422/56 |
| 5,948,895 | A | * 9/1999 | Sugiyama et al. | .......... 530/395 |

* cited by examiner

Primary Examiner—Maureen M. Wallenhorst
(74) Attorney, Agent, or Firm—Reed Smith LLP

(57) ABSTRACT

A control serum for a dry process is provided that does not show misfit in measurement values by the dry process and a wet process. The above-mentioned control serum is obtained by freezing or freeze-drying a control serum without dialysis.

3 Claims, 2 Drawing Sheets

◇:refrigerated human serum ☐:refrigerated pooled serum
△:frozen pooled serum ✕ :dialyzed pooled serum ○ :refrigerated human serum  □ :refrigerated pooled serum
△ :frozen pooled serum      × :dialyzed pooled serum ○ :refrigerated human serum  □ :refrigerated pooled serum
△ :frozen pooled serum      × :dialyzed pooled serum

CONTROL SERUM FOR DRY ANALYTICAL ELEMENT

CROSS-REFERENCE TO RELATED APPLICATIONS

This application is a continuation application claiming priority to U.S. application Ser. No. 10/159,081, filed on May 29, 2002, now abandoned.

BACKGROUND OF THE INVENTION

This invention relates to a control serum useful in a field of clinical diagnosis using a dry analytical element.

Diagnosis of human illness by analyzing a specimen such as blood or urine has been prosecuted for a long period of time. To analyze an analyte(s) in the specimen, there are two processes. That is to say, a wet process in which an aqueous solution is prepared by adding reagents necessary for a designed analysis and a specimen in water to produce some reaction between them, and a dry process in which a specimen is supplied to a layer (for example, a layer of gelatin) containing reagents in advance in a dry state to produce some reaction between them in the layer.

When either of the above-mentioned methods is carried out, a control serum is employed to draw up a calibration curve or to quality control of analysis. Generally, the control serum is prepared using human serum or bovine serum from which fibrin is eliminated as raw material and then removing calcium ions from it used for elimination of fibrin through a dialysis processing. In the dialysis processing, some components with low molecular weight are also lost at the same time. Then, a necessary component (e.g. pure substance, an enzyme or the like) is added to adjust concentration of the serum. Further, a surfactant, an antiseptic agent (an antibiotic or the like) or an activating agent (NAC for CK or the like) is sometimes added.

Conventionally, a control serum based on the serum that has been once dialyzed is used in either of two processes above mentioned. The control serum is manufactured by following steps in outline. Only plasma is collected as a component of blood using a blood collecting tube containing an anticoagulant in it. Then plural plasma samples thus collected are mixed to prepare pooled plasma. The pooled plasma is added with $Ca^{2+}$ ions and subjected to processing of elimination of fibrin to obtain pooled serum rich in $Ca^{2+}$ ions. Then, the pooled serum rich in $Ca^{2+}$ ions is dialyzed to remove excess $Ca^{2+}$ ions to prepare the pooled serum for raw material of the control serum.

However, when the control serum prepared by the above-mentioned process is used, such problem has occurred that results of measurement of the same specimen obtained by the wet process and the dry process show misfit each other. An actual example for UA is shown in FIG. 1. In FIG. 1, ▲ illustrates the result obtained using the control sample of the Japan Medical Association, and ○ illustrates the result obtained using human raw serum, respectively. In the case where the accuracy control sample of the Japan Medical Association is used, the result of the dry process shows higher value than that of the wet process. Though not shown in the figure, results concerning BUN and CRE were similar.

One method to solve the problem is disclosed in JP 2000-131323 A. According to the method, reactivity of a control serum similar to that of a fresh human serum is assured by adding buffering agents such as bicarbonates, 6-aminocaprone or the like to commercially available control serums. However, some problems still remain when utilizing the method, such that prescription may be changed when a commercially available control serum is displaced by another one, an additional processing is required and it is difficult to say that availability for the all test necessary for clinical analysis has been confirmed or the like.

SUMMARY OF THE INVENTION

The purpose of this invention is to provide a control serum which enables to obtain identical quantitative results in both wet and dry analytical processes for a lot of tests necessary for clinical analysis.

The above-mentioned purpose has been achieved by a control serum prepared from a frozen or freeze-dried pooled serum (a mixture of plural serum samples obtained by centrifugation of a lot of whole blood specimens collected).

DETAILED DESCRIPTION OF THE INVENTION

Figure 1:
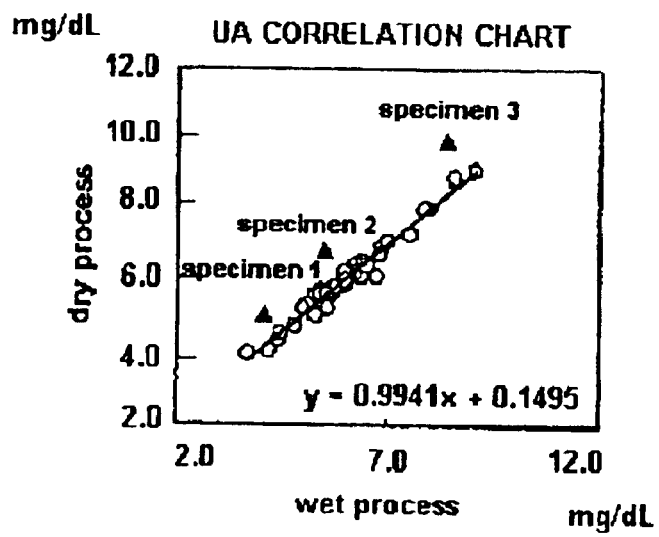
FIG. 1 shows misfit of values measured by the dry process and the wet process using the accuracy control material of the Japan Medical Association. The test item is UA.

The control serum according to the present invention is obtained by freezing or freeze-drying a pooled serum. Condition for a freezing processing is −20° C. or less, preferably −40° C. or less. Drying condition in a freeze-dry processing depends on an amount of a frozen serum to be processed and it is preferable that the freeze-dry processing is completed in a short period of time.

First of all, description will be made as to effects of dialyzing serum, though it is not an embodiment of the present invention. The inventors of the present invention prepared a dialyzed serum to demonstrate effects of dialysis by dialyzing a pooled serum, and then adding lost low molecular weight components to adjust concentration of the serum. Detailed conditions of dialysis etc. will be shown later as a reference example. Table 1 shows conformity of values measured by the dry process and the wet process respectively using the above mentioned dialyzed serum as the control serum. It is obvious from Table 1 that measured values are different for a lot of tests. That is to say, it is understood that so called "matrix effect" (chemically, various effects that have some influences on a measured value by interfering with measurement, which are brought about by principle of measurement, composition of reagents, denaturalization of samples, additives and the like) occurs.

The above-mentioned results suggest that it is important to use serum that is not dialyzed as the control serum to obtain same quantitative results using the dry process and the wet process. The present invention has been accomplished based on the information.

Using the control serum according to the present invention, which is prepared by freezing or freeze-drying the pooled serum, the same results are obtained by the dry process and the wet process for the almost all tests that can be analyzed by the dry process, as shown bellow by examples.

The pooled serum preferably used to carry out the present invention is manufactured by general steps described bellow. First of all, whole blood is collected using a blood-drawing tube that does not contain any anti-coagulating agent. The whole blood is separated into serum and clot by means of centrifugation. Pluralities of serum thus obtained are mixed to prepare the pooled serum. Such pooled serum is called as "the true serum" among persons skilled in the art. Now, the performance of the control serum according to the present invention is exemplified by examples.

EXAMPLES

Reference Example

1. Preparation of Dialyzed Serum

Pluralities of whole blood were collected from pluralities of normal human using blood-drawing tubes with a serum separator, respectively. Then the respective whole bloods were dialyzed to obtain pluralities of serum and obtained plural kinds of serum were mixed to prepare a pooled serum. Three mL of the pooled serum was poured into a cassette for dialysis (Slide-A-Lyzer manufactured by Pierce company, U.S.A., of which cutoff molecular weight was 10,000). Then dialysis was carried out with stir using 500 mL of physiological saline solution (pH 7.4) buffered with 0.01M phosphoric acid as a dialyzing fluid in a refrigerator at 4° C. for 114 hours. The dialyzing fluid was replaced with a new one after 18 hours from the start of the dialysis. The pooled serum was gotten out of the cassette after the dialysis. Then, since content of water was increased by the dialysis, the pooled serum was subjected to a condensation processing with a cassette for condensation (VIVAPORE; manufactured by VIVASCIENCE company, U.S.A.) to reduce the volume to about 3 mL. Since low molecular weight components were lost from the serum by dialysis, glucose, urea, uric acid, creatinine, magnesium chloride and calcium chloride were added to the serum to make concentration of these components be adjusted approximately equal to concentration of the original pooled serum. The pooled serum before use was stored in the refrigerator.

2. Measurement of Sample

The dialyzed serum prepared in the step 1 above mentioned and twenty specimens of raw human serum, respectively, were measured by an apparatus described bellow.

2-1. Dry Process

FUJI DRI-CHEM AUTO SLIDE (trademark; manufactured by FUJI PHOTO FILM CO., LTD; hereinafter referred to as "FDC") and FUJI DRI-CHEM AUTO5 (trademark; special purpose machine for FDC manufactured by FUJI PHOTO FILM CO., LTD) were used.

2-2. Wet Process

HITACHI MODEL 7170 AUTOMATIC ANALYZER (trademark; manufactured by Hitachi, Ltd.) and special purpose reagents were used. Further, HITACHI MODEL 710 AUTOMATIC ELECTROLYTES ANALYZER (trademark; manufactured by Hitachi, Ltd.) was used for measurement of potassium.

3. Evaluation Method

Reactivity of each serum was investigated by carrying out correlation analysis while taking the values measured by the wet process as Xs and the values measured by the dry process as Ys. In the correlation chart, specimens, which showed the misfit from a normal human serum group, were evaluated that the reactivity of them were different depending on a case whether the dry process was used or the wet process was used.

4. Summary of the Measurement Results

Figure 2:
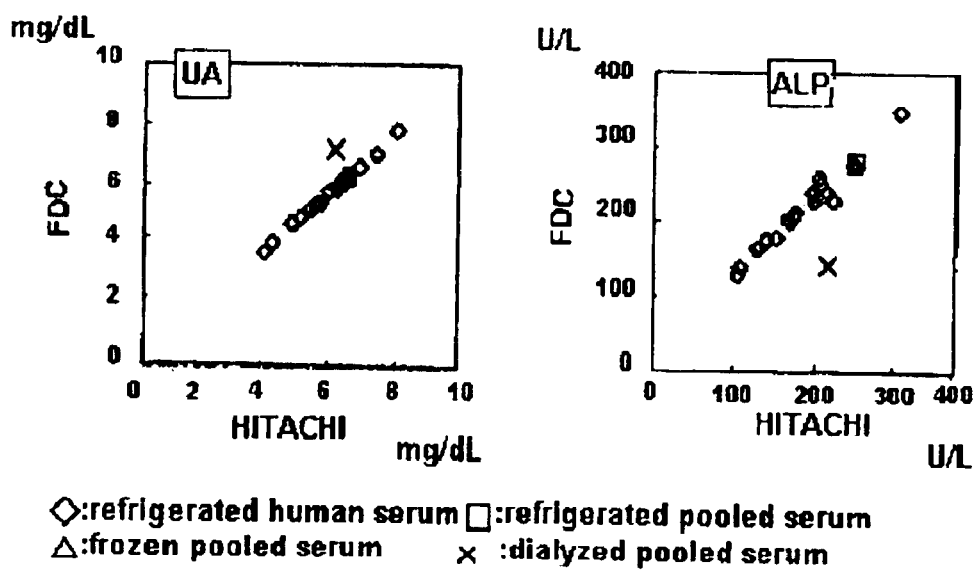
FIG. 2 shows misfit of values measured for UA and ALP, respectively, using dialyzed serum.
Figure 3:
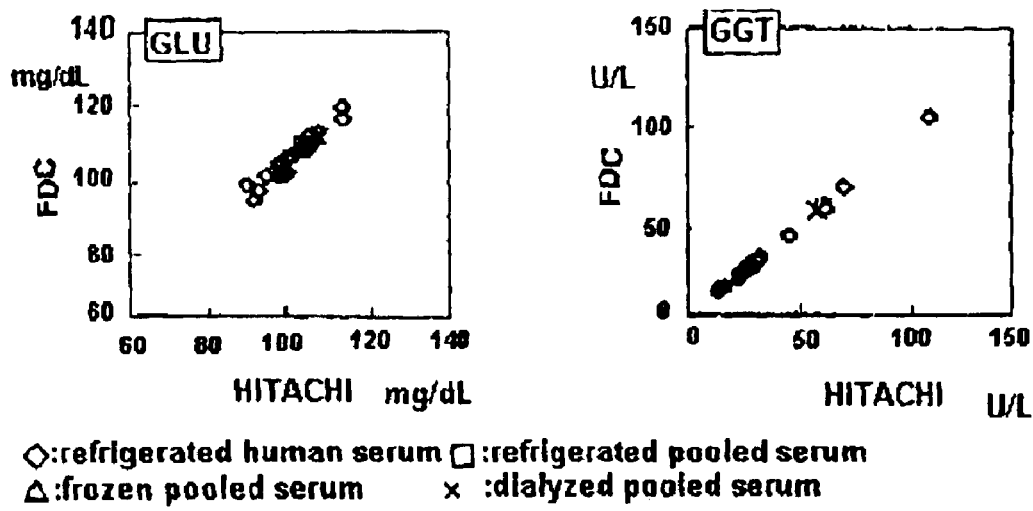
FIG. 3 shows conformity of values measured for GLU and GGT, respectively, using a dialyzed pooled serum.

Measurement results are shown in Table 1. Further, misfit of measurement results for UA and ALP are shown in FIG. 2. From Table 1, it is understood that misfit occurred between the measurement results of the dry process and the wet process, respectively, for a lot of tests. On the other hand, the measurement results of GLU and GGT, respectively, are shown in FIG. 3 as an example that does not show misfit. The abbreviated notations of respective tests are well known to persons skilled in the art and a detailed description of them is omitted.

Example 1

Figure 4:
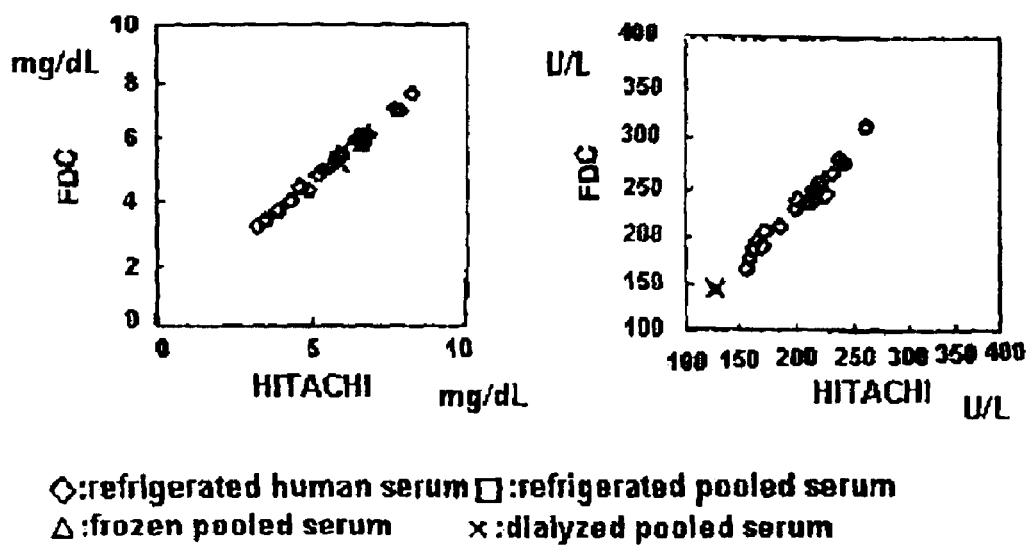
FIG. 4 shows conformity of values measured for UA and ALP, respectively, using a frozen pooled serum or a freeze-dried pooled serum.

The pooled serum prepared in the reference example was frozen by storing it in a freezer kept at −80° C. It was molten at room temperature for use. Then, measurement was carried out in the same manner as described in the paragraph 2 of the reference example and evaluation was carried out in the same manner as described in the paragraph 3 of the reference example. Results of the evaluation are shown in Table 1. It is understood that the dry process and the wet process give the same measurement results for the all tests measured. Further, examples of UA and ALP that indicate the same measurement results are shown in FIG. 4, though the measurement results of them showed misfit in the reference example.

Example 2

Three mL of the pooled serum prepared in the reference example was charged into an eggplant type flask (50 mL in volume), rapidly frozen with liquidized nitrogen, and subjected to vacuum drying by a vacuum pump for about 20 hours. The pooled serum after drying was solved for use by adding 3 mL of purified water. Then, measurement and evaluation were carried out in the same manner as described in the example 1. Results are shown in FIG. 1. It is understood that the dry process and the wet process give the same measurement results for the all tests measured. Further, examples of UA and ALP that indicate the same measurement results are shown in FIG. 4, though the measurement results of them showed misfit in the reference example.

Thus, when the control serum according to the present invention is used, the same measurement values can be obtained by the dry process as the measurement results obtained by the wet process.

TABLE 1

Synoptical Table of Measurment Results

| | Processing of Serum | | |
|---|---|---|---|
| Inspection Item | Dialysis (reference example) | Frozen (Example 1) | Feeze-dried (Example 2) |
| GLU | ± | ± | ± |
| BUN | ↑ | ± | ± |
| UA | ↑ | ± | ± |
| TCHO | ↑ | ± | ± |
| TG | ND | ± | ± |
| CRE | ↓ | ± | ± |
| TP | ± | ± | ± |
| ALB | ↓↓ | ± | ± |
| TBIL | ± | ± | ± |
| HDL-C | ↑ | ± | ± |
| IP | ND | ± | ± |
| DBIL | ± | ± | ± |
| Mg | ↓ | ± | ± |
| GGT | ± | ± | ± |

TABLE 1-continued

Synoptical Table of Measurment Results

| | Processing of Serum | | |
|---|---|---|---|
| Inspection Item | Dialysis (reference example) | Frozen (Example 1) | Feeze-dried (Example 2) |
| GOT/AST | ± | ± | ± |
| GPT/ALT | ±~slightly ↑ | ± | ± |
| CPK | ± | ± | ± |
| LDH | ±~slightly ↓ | ± | ± |
| ALP | ↓↓ | ± | ± |
| AMYL | ± | ± | ± |
| LAP | ± | ± | ± |
| CKMB | ↓↓ | ± | ± |
| CHE | ± | ± | ± |
| K | ND | ± | ± |
| CRP | ± | ± | ± |

↑: higher value
↓: lower value
±: no change
ND: no data

What is claimed is:

1. A method of measuring a blood component in a control serum using a dry analytical process comprising the steps of: applying a control serum to a dry analytical element containing reagents for reading with the blood component, and measuring the reaction between the reagents and the blood component, wherein said control serum is prepared from fibrin-free or fibrin-removed serum without performing dialysis, followed by freezing or freeze drying, and further wherein said blood component is selected from the group consisting of blood urea nitrogen, uric acid, total cholesterol, creatinine, albumin, high density lipoprotein cholesterol, magnesium, alkaline phosphatese, and creatine kinase subunit MB.

2. The method of claim 1, wherein said blood component is uric acid or alkaline phosphatase.

3. The method of claim 1, wherein said fibrin has been removed in the presence of calcium ions.

* * * * *